US012564433B2

(12) United States Patent
Zhang et al.

(10) Patent No.: US 12,564,433 B2
(45) Date of Patent: Mar. 3, 2026

(54) APPARATUSES AND METHODS FOR ABLATION TREATMENTS INCLUDING PROBES WITH HANDLE HEATING

(71) Applicant: Varian Medical Systems, Inc., Palo Alto, CA (US)

(72) Inventors: Hongxuan Zhang, Austin, TX (US); Vineel Vallapureddy, Plymouth, MN (US); Ryan Lee Medema, Georgetown, TX (US)

(73) Assignee: Varian Medical Systems, Inc., Palo Alto, CA (US)

( * ) Notice: Subject to any disclaimer, the term of this patent is extended or adjusted under 35 U.S.C. 154(b) by 746 days.

(21) Appl. No.: 17/819,106

(22) Filed: Aug. 11, 2022

(65) Prior Publication Data

US 2024/0050142 A1     Feb. 15, 2024

(51) Int. Cl.
A61B 18/02       (2006.01)
A61B 18/04       (2006.01)
A61B 18/00       (2006.01)

(52) U.S. Cl.
CPC .... *A61B 18/02* (2013.01); *A61B 2018/00041* (2013.01); *A61B 2018/00577* (2013.01); *A61B 2018/00589* (2013.01); *A61B 2018/00595* (2013.01); *A61B 2018/00714* (2013.01); *A61B 2018/00863* (2013.01); *A61B 2018/0293* (2013.01)

(58) Field of Classification Search
CPC ......... A61B 18/02; A61B 2018/00577; A61B 2018/00589; A61B 2018/00595; A61B 2018/00636; A61B 2018/00642; A61B 2018/00696; A61B 2018/00714; A61B 2018/00744; A61B 2018/00773; A61B 2018/00791; A61B 2018/00797; A61B 2018/00827; A61B 2018/00863; A61B 2018/00922; A61B 2018/00958; A61B 2018/0262; A61B 2018/0293; A61B 2018/044

See application file for complete search history.

(56) References Cited

U.S. PATENT DOCUMENTS

| | | | | | |
|---|---|---|---|---|---|
| 3,507,283 | A | * | 4/1970 | Thomas, Jr. ........... | A61B 18/02 606/24 |
| 3,993,075 | A | * | 11/1976 | Lisenbee ................ | A61B 18/02 606/26 |
| 6,039,730 | A | * | 3/2000 | Rabin ................... | A61B 90/17 606/22 |

(Continued)

FOREIGN PATENT DOCUMENTS

| | | |
|---|---|---|
| WO | 2010075438 A1 | 7/2010 |
| WO | 2024036253 A1 | 2/2024 |

OTHER PUBLICATIONS

International Search Report and Written Opinion for PCT/US2023/071988 dated Nov. 24, 2023, 18 pages.

*Primary Examiner* — Daniel W Fowler
(74) *Attorney, Agent, or Firm* — Morgan, Lewis & Bockius LLP; Manita Rawat

(57) ABSTRACT

A probe for performing a cryoablation treatment that includes a handle with a heater configured to heat a fluid and a needle connected to the handle and extending therefrom to a distal end. The needle includes a pathway configured to move the fluid from the handle toward the distal end to heat the needle.

23 Claims, 7 Drawing Sheets

(56)     References Cited

U.S. PATENT DOCUMENTS

| | | | | |
|---|---|---|---|---|
| 6,106,520 | A * | 8/2000 | Laufer | ............... A61B 18/1492 606/49 |
| 6,270,493 | B1 * | 8/2001 | Lalonde | ................. A61B 18/02 606/23 |
| 2001/0035189 | A1 | 11/2001 | Dobak, III | |
| 2003/0014095 | A1 | 1/2003 | Kramer et al. | |
| 2007/0118104 | A1 * | 5/2007 | Wallace | ................. A61B 18/18 606/41 |
| 2010/0168725 | A1 * | 7/2010 | Babkin | .................. A61B 18/02 606/21 |
| 2010/0204688 | A1 * | 8/2010 | Hoey | ..................... A61B 18/04 606/27 |
| 2010/0274237 | A1 * | 10/2010 | Yamakawa | .............. A61B 5/24 606/23 |
| 2011/0178514 | A1 | 7/2011 | Levin et al. | |
| 2011/0245821 | A1 * | 10/2011 | Zachman | ............... A61B 18/02 606/21 |
| 2012/0136350 | A1 * | 5/2012 | Goshgarian | ........ A61B 18/1492 606/41 |
| 2012/0265189 | A1 * | 10/2012 | Davis | .................... A61B 18/02 606/22 |
| 2014/0005650 | A1 | 1/2014 | Burnett et al. | |
| 2016/0249970 | A1 | 9/2016 | Yu et al. | |
| 2017/0165002 | A1 | 6/2017 | Sharma et al. | |
| 2019/0175245 | A1 * | 6/2019 | Henne | .................... A61B 18/04 |
| 2020/0100776 | A1 * | 4/2020 | Blumenkranz | .... A61B 5/02042 |

* cited by examiner

APPARATUSES AND METHODS FOR ABLATION TREATMENTS INCLUDING PROBES WITH HANDLE HEATING

FIELD

The present disclosure relates to apparatuses and methods for ablation treatments that include probe handle heating and/or sensing. The present disclosure relates to apparatuses and methods that may be used to perform cryo and/or heating operations during ablation treatments.

BACKGROUND

This section provides background information related to the present disclosure which is not necessarily prior art.

Systems and methods for providing ablation treatments generally include the introduction of a probe at or near a target tissue in a patient. The target tissue may be an abnormal or undesirable tissue such as a tumor. The ablation treatment is performed to destroy the target tissue. In addition to destroying the target tissue, it is desirable to minimize damage or harm to healthy tissues that may be located near to the target tissue.

One type of ablation treatment is a cryoablation treatment. Cryoablation treatments may include cryoablation probes that are introduced at or near the target tissue in the patient. A cryoablation system may include an extremely cold cryogen (liquid, gas, or mixed phase) that may be passed through the probe in thermal contact with the target tissue. Heat from the tissue passes from the tissue, through the probe, and into the cryogen that removes heat from the targeted tissue. This removal of heat causes tissue to freeze, resulting in the destruction of the targeted tissue. When the tissue freezes, ice forms typically in an iceball. The iceball may be in the form a sphere, ellipsoid or other shape. It is desirable to perform cryoablation treatments such that the target tissue is completely frozen and that the freezing of surrounding tissues and/or body structures is minimized.

The probe may also be used during treatments to heat the probe and/or a localized region at the target tissue. Such heating operations may be used to perform various operations such as to promote coagulation, track heating, or others. It can also be desired to obtain measurement information regarding the conditions at or around the probe, such as temperature information, during ablation treatments.

Traditional or existing systems and methods suffer from various drawbacks. It can be difficult, for example, to provide suitable probes and related methods that can provide cryo, heating, and sensing capability. All of these functions may require elements and structures in the probe but it is desirable to minimize the size of the probe that is inserted into a patient to minimize the impact on the patient and/or minimize harm to healthy tissues. There exists a need, therefore, for improved apparatuses and methods that can provide cryo, heating, sensing, and related functionalities in a probe that minimizes the impact of the ablation treatment on the patient.

SUMMARY

This section provides a general summary of the disclosure, and is not a comprehensive disclosure of its full scope or all of its features.

In various embodiments of the present disclosure, apparatuses and methods for performing ablation treatments are provided. The cryoablation systems of the present disclosure include probes with improved capability over existing or traditional apparatuses and methods. The methods and probes of the present disclosure may incorporate a heater in the handle of the probe that can be used to heat the needle for various purposes. The heater positioned in the handle allows improved heating cycles that can achieve temperatures necessary for thaw cycles, coagulation cycles, cauterization cycles, pain relief cycles and the like. These heating cycles can be used in addition to freezing cycles during cryoablation treatments. The probes and the cryoablation systems of the present disclosure may also incorporate closed loop sensing and monitoring functionality to allow the probe to automatically adjust operating parameters in real-time during ablation treatments to achieve improved performance over traditional systems and methods.

In some embodiments of the present disclosure, a probe for performing a cryoablation treatment is provided. The probe may include a handle with a heater configured to heat a fluid and a needle connected to the handle and extending therefrom to a distal end. The needle may include a pathway configured to move the fluid from the handle toward the distal end to heat the needle.

In one aspect, the fluid may be a cryogen configured to alternatively cool the needle when the heater is not activated and to heat the needle when the heater is activated.

In another aspect, the pathway is further configured to move a cryogen from the handle toward the distal end to cool the needle.

In another aspect, the cryogen and the fluid are different fluidic materials.

In another aspect, the fluid and the cryogen are the same fluidic material.

In another aspect, the handle may include a conduit in thermal contact with the heater. The fluid may be heated by the heater as the fluid moves through the conduit.

In another aspect, the heater may be positioned around the conduit.

In another aspect, the conduit may be positioned around the heater.

In another aspect, the heater may be a resistive heater.

In another aspect, the heater may be one of a magnetic heater and a fiber laser heater.

In another aspect, the probe may also include one or more measurement points positioned on the needle.

In some embodiment of the present disclosure a system for performing a cryoablation treatment is provided. The system may include one or more ablation computing devices coupled to one of the probes described above. The one or more ablation computing devices may be configured to selectively heat and cool the needle.

In one aspect, the one or more ablation computing devices may be further configured to selectively activate the heater to heat the needle to a predetermined temperature range.

In another aspect, the one or more ablation computing devices may be configured to activate the heater when a bleeding condition is detected.

In another aspect, the one or more ablation computing devices may be configured to activate the heater when the needle is being moved from a treatment position in a patient and to de-activate the heater when the needle has been moved a predetermined distance from the treatment position.

In some embodiments, a method operating a cryoablation probe is provided. The method may include cooling a needle of the probe to form ice at a target tissue and heating the needle of the probe using a heater positioned in a handle of the probe.

In one aspect, the step of heating the needle of the probe may include heating a fluid that moves through the handle to a distal end of the needle. The fluid may be in thermal communication with the heater in the handle of the probe.

In another aspect, the step of cooling the needle may include moving a cryogen from a cryogen source through the handle and toward a distal end of the needle.

In another aspect, the method may also include obtaining measurement information regarding operating conditions of cryoprobe, comparing measurement information to a treatment plan, and adjusting the operating conditions of the cryoprobe if the measurement information deviates from the treatment plan.

In another aspect, the step of heating the needle may include denaturing proteins in tissue proximate the needle to reduce a likelihood of contaminating healthy tissues.

In another aspect, the step of heating the needle is performed after the step of cooling the needle in order to allow the needle to be removed from the ice.

In another aspect, the step of heating the needle is performed to promote coagulation of blood when a bleeding condition is detected.

In another aspect, the step of heating the needle is performed when the needle is moved from a first position to a second position.

In another aspect, the step of heating the needle is initiated when the needle is positioned at an initial position at the target tissue, and the heating of the needle is automatically stopped when the needle is moved a predetermined distance.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
FIG. 1 is a diagram illustrating an example ablation system in accordance with some embodiments of the present disclosure.
Figure 1:
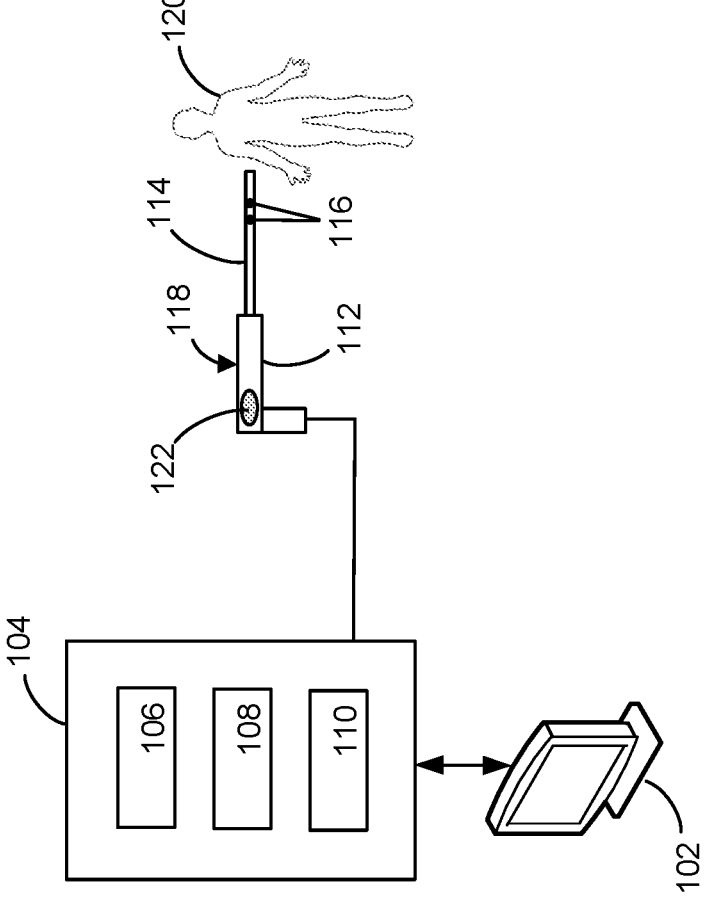

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In some embodiments of the present disclosure, a cryoablation system and probe is provided. The cryoablation system may allow a cryoablation treatment to be performed. During example treatments, the needle of the cryoprobe can be positioned at or near a target tissue (e.g., a tumor or other abnormal tissue). The needle can be cooled to cause ice to form at the target tissue to destroy the target tissue. The cryoablation systems and probed of the present disclosure may also allow a heating cycle to be performed in which the needle of the probe is heated to elevated temperatures. The heating cycles may cause the ice that is formed at the target tissue to melt to allow removal of the needle from the treatment position. The heating cycles may also be used to denature proteins at the location of the needle so that abnormal cells such as cancerous cells are not migrated from one position to another and/or to healthy tissue if the needle must be repositioned during treatment. In other circumstances, the heating cycle may be used to promote coagulation when a bleeding condition occurs during an ablation treatment. In still other circumstances, the heating cycle can be used to prevent bleeding conditions when the needle is removed from an initial or treatment position.

The probes of the present disclosure may include a handle from which the needle extends. A heater can be positioned in the handle portion (as opposed to in the needle or in other locations) of the probe. This can allow the needle to be heated without the need for enlarging the size of the needle. The needle, in various examples, may have an outer diameter of 1.2 mm or less. In other examples, the needle may have an outer diameter of 1 mm or less. In still other examples, the needle may have an outer diameter of less than 1 mm. In other examples, other size needles can also be used.

The systems and probes of the present disclosure are improvements over existing and traditional designs and methods. In existing systems, the heater may be located in the needle that may cause the size of the needle to be larger than desired. Such larger sizes may cause more damage to healthy tissues and/or cause more bleeding than the probes of the present disclosure. Traditional systems and probes also do not include the heating capabilities of the probes of the present disclosure to allow for a reduction in the likelihood of contamination of healthy tissues. Traditional systems and probes also do not include the control systems and/or related methods described in the present disclosure that allow for improved effectiveness and repeatability of treatment. In addition, ablation treatments using the probes, systems, and methods of the present disclosure can take shorter treatment times and reduce the impact of the treatment on healthy tissues.

Turning now to FIG. 1, and example cryoablation system 100 is shown. The cryoablation system 100 may include a cryo controller 104 that is coupled to an ablation computing device 102 and to a probe 118. The cryoablation system 100 may be configured to perform cooling and heating cycles.

The cryo controller 104 may include a cryo system 106, a heating system 108, and a measurement system 110 that will be further described.

The cryo system 106 can deliver a cryogen to the probe 118. The cryogen can remove heat from the probe and from tissue that may be located near the probe 118 when a needle 114 of the probe 118 is positioned in a desired location in the patient 120. The needle 114 may be positioned, for example, at or near a target tissue such as a tumor, lesion, or other abnormal tissue. The cryo system 106 can cause an iceball (of various suitable shapes and sizes) to be produced at a distal end of the needle 114 that destroys the target tissue. The cryogen may be various suitable fluids. In one example, the cryo delivery system 106 is configured to deliver liquid and/or gaseous nitrogen to the probe 102. In other examples, argon, helium, oxygen or other liquids and gasses may also be used. The cryo system 106 in combination with the probe 118 can be configured in various suitable manners such as a Joules-Thompson cryoablation systems, critical or near-critical cryoablation systems, or others.

The heating system 108 can be configured to allow the probe 118 to heat the needle 114. The heating system 108 may include a heating fluid such as a liquid or gas such as argon, helium, nitrogen, oxygen, or other liquid or gas to be passed from a fluid source (e.g., tank, container, etc.) to a handle 112 of the probe 118. The heating fluid may pass through the handle 112 and to the distal end of the needle 114. The heating fluid can be heated using a heater 122 that is located in the handle 112 of the probe 118. In some examples, the cryo system 106 and the heating system 108 can be combined or integrated to use the same cryogen and/or heating fluid. In other examples, the cryogen that is used to cool the needle 114 of the probe 118 is different from the heating fluid that is used to heat the needle 114 of the probe 118.

The cryo controller 104 may also include the measurement system 110. The measurement system 110 can be coupled to the probe 118 and/or to other measurement devices, sensors, imaging systems, and the like that can collect measurement information regarding the operating conditions of the probe 118, health and/or vital information for the patient 120, or other information regarding operation of the cryoablation system 100. The measurement system 110 can obtain measurement information from the various sensors, devices, system and the like. The measurement system 110 may include, for example, a bus or other device and/or a measurement acquisition device to convert the signals from the various sensors, devices, systems and the like to flow rates, pressures, temperatures, or other measurements that may be used to control and adjust the operation of the probe 118 during an ablation treatment.

As shown, the cryo controller 104 may be coupled to the ablation computing device 102. While the ablation computing device 102 is shown separately from the cryo controller 104, the ablation computing device 102 and the cryo controller 104 may be combined or integrated together. The ablation computing device 102 may be any suitable computing device with processing capability and/or memory to allow the ablation computing device 102 to perform one or more steps of the various methods and functionality of the cryoablation system 100 described in the present disclosure. In various examples, the ablation computing device 102 may be a workstation, desktop computer, laptop, tablet, server, programmable logic controller, or the like.

As further shown, the probe 118 may include a handle 112. The handle 112 is shown as a right-angle handle that includes two portions oriented at a 90 degree angle to one another. The handle 112 can be configured in other manners and may be substantially linear in shape. As shown, the handle 112 of the probe 118 may include the heater 122. In various examples, the heater 122 can comprise various suitable heating elements that can be used to heat a fluid that moves from the heating system 108 to the probe 118. The heater 122 may, for example, comprise a resistive heater that is coupled to a power source that can be activated to generate heat when a current is provided to the resistive heater. In other examples, a coil magnetic heater, a fiber laser heater or other heating elements can be used.

The needle 114 of the probe 118 can extend from the handle 112 toward a distal end. The probe 118 and/or the needle 114 can include multiple measurement points 116 positioned on, in or around the needle 114. The measurement points 116 can be electrical pads, sensors, or other features that can collect measurement information. The measurement points 116 can collect impedance measurements, pressure measurements, voltage measurements, flow measurements, current measurements, temperature measurements or other measurements that can be used to control and/or determine an operating condition of the cryoablation system 100. In some examples, as shown, the measurement points 116 can be located at different axial positions along the needle 114. In other examples, the measurement points can be located at different circumferential positions around the needle 114 in addition to at different axial locations.

Figures 2A, 2B, 2C:
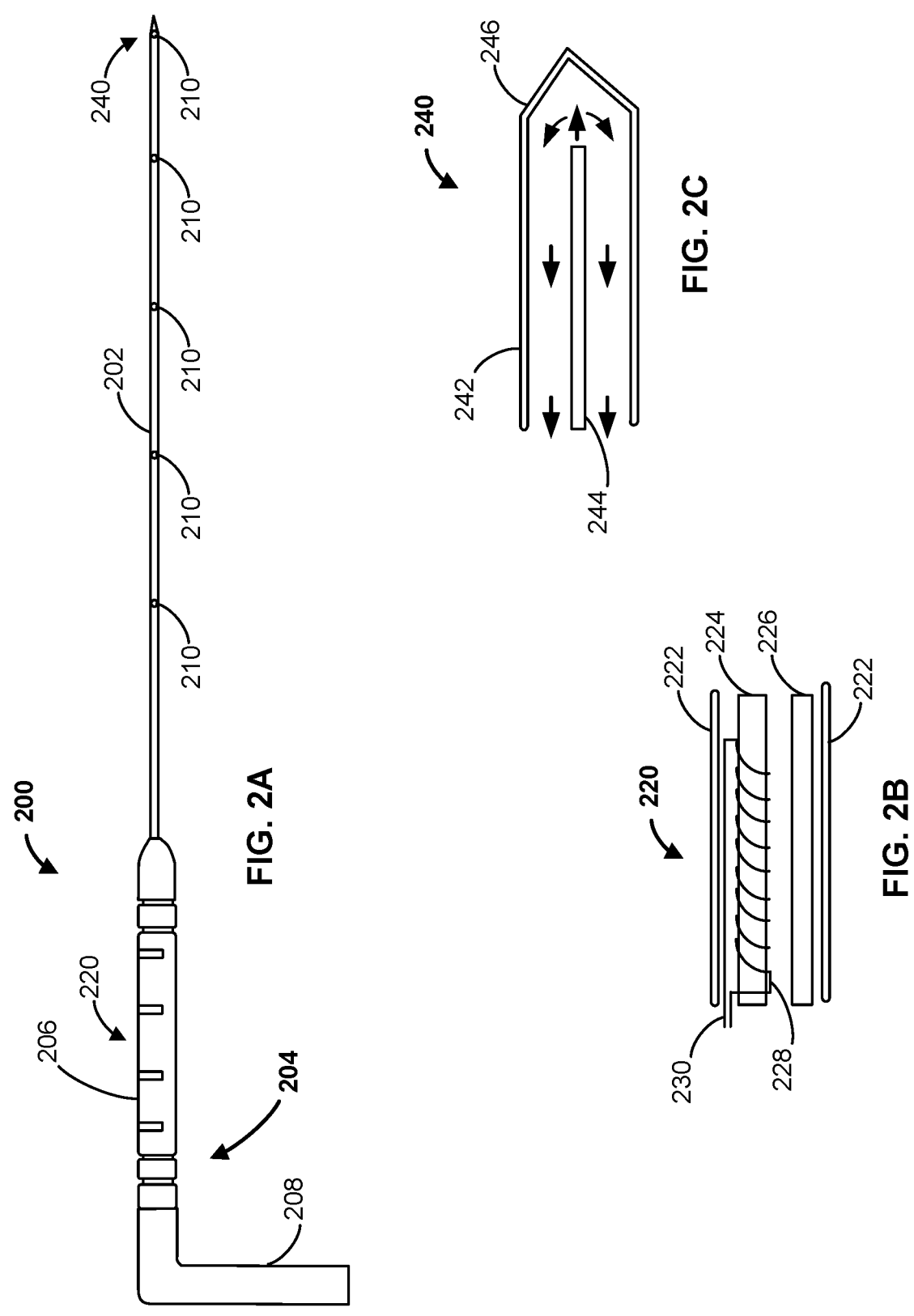
FIG. 2A is a side view of an example probe in accordance with some embodiments of the present disclosure.
FIG. 2B is a side view of an example heater that can be positioned in the handle of the probe of FIG. 2A.
FIG. 2C is side view of an example tip of the needle of the probe of FIG. 2A.

Turning now to FIGS. 2A-C, an example probe 200 is shown. The probe 200 can be similar to the probe 102 previously described. As shown, the probe 200 can include a handle 204 can include a first portion 206 and a second portion 208. the first portion 206 can be axially aligned with the needle 202. The second portion 208 can be connected to the first portion 206 and be oriented 90 degrees from the first portion 206. In other examples, the first portion 206 can be oriented at different orientations, such as other angles, relative to the second portion 208. In still other examples, the handle 204 may only include a portion that is aligned with the needle 202.

The handle 204 may be molded of a suitable plastic material and can include various structures to allow or facilitate the operation of the cooling cycles and the heating cycles of the probe 200. The handle 204 may, for example, include a heater that can be used to heat the needle 202. The handle 204 may also include, in various examples, insulation to allow an operator to grip the probe 200 during a freezing cycle. A vacuum chamber and/or an insulating material can be included in the handle 204. The handle 204 may also be used to enclose various conduits, wires, or other pathways that can allow a cryogen, heating fluid, and/or other electrical paths to pass from the needle 202 to the cryo controller 104 and/or the ablation computing device 102.

In one example, the structure as shown in FIG. 2B, can be included in the first portion 206 and/or the second portion 208 of the handle 204. The heater 220 can be enclosed in a housing 222 of the handle 204. The housing 222 can be an outer wall of the handle 204 and can define an internal cavity in which various structures can be enclosed. The housing 222 may be shaped in various manners such as in a cylindrical, square, rectangular, oval, or other shape.

The needle 202 may extend from the handle 204 to a distal end 240. The needle 202 may be elongated and have a linear shape. In other examples, the needle 202 may be flexible, curved or have other shapes. The needle 202 is of sufficient strength to allow the needle 202 to be inserted into a patient. The needle 202 may have an outer size that is less than the outer size of the handle 204. This may allow the heater 220 to be positioned in the handle 204, rather than in the needle 202, so that the outer size of the needle 202 does not need to be increased. In various examples, the needle 202 can have a suitable outer size or outer diameter so as to minimize the impact of the ablation treatment on the patient when the needle 202 is inserted into a patient and positioned proximate the target tissue. In some examples, the needle 202 may be made of a stainless steel or other alloy material. In other examples, the needle 202 may be made of a ceramic or other composite material. In still other examples, the needle 202 can be made of a combination of materials with different sections of materials joined together. The needle, in various examples, may have an outer diameter of 1.2 mm or less. In other examples, the needle may have an outer diameter of 1 mm or less. In still other examples, the needle may have an outer diameter of less than 1 mm. In other examples, other size needles can also be used.

The needle 202 may include one or more measurement points 210. The measurement points 210 may be similar to the measurement points 116 previously described. The measurement points 210 may be positioned on, in or around the needle 202. The measurement points 210 can be electrical pads, sensors, or other features that can collect measurement information. The measurement points 210 can collect impedance measurements, pressure measurements, voltage measurements, flow measurements, current measurements, temperature measurements or other measurements that can be used to control and/or determine an operating condition of the cryoablation system 100. In some examples, as shown, the measurement points 210 can be located at different axial positions along the needle 202 between the handle 204 and the distal end 240. In other examples, the measurement points can be located at different circumferential positions around the needle 202 in addition to at different axial locations.

The housing 222 may enclose an input conduit 224 and output conduit 226. The input conduit 224 may allow the cryogen and/or the heating fluid to flow from the cryo controller 104 to the distal end 240 of the needle 202. In some examples, the cryogen and the heating fluid may be the same fluid or gas. In other examples, the cryogen and the heating fluid may be different. The output conduit 226 can be positioned parallel to the input conduit 224 and allow the cryogen and/or the heating fluid to move away from the needle 202 back to an exhaust or to the cryo controller 104 for re-use. The heater 220 can be positioned in thermal communication with the input conduit 224. In this manner, the heater 220, when activated, can heat the fluid that is moving through the input conduit 224. In the example shown, the heater 220 can be configured as a resistive heating element that include a plurality of coils that are wrapped around the input conduit 224. The heating elements can be coupled to the heating system 108 via the leads 228 and 230. When an electrical power is provided to the heating element via the leads 228 and 230, the heater 220 can heat and transfer heat to the fluid moving through the input conduit 224.

The amount of heat that is transferred to the fluid in the input conduit can be controlled by the cryo controller 104 via the heating system 108 to heat the fluid to predetermined temperature or to a predetermined temperature range. The heater 220 can be controlled via the power signal that is provided to the heater 220. A predetermined power profile can be delivered and modified to heat the fluid as desired using pulse width modulation (PWM), a duty cycle, amplitude modulation, frequency modulation, and/or predetermined current and voltage profiles.

In other examples, the heater 220 can be configured in other manners to transfer thermal energy to the fluid in the input conduit 224. In other examples, the heater 220 can be a magnetic coil heater, a fiber laser heater, or other heaters. Since the heater 220 is positioned in the handle 204, there are less limitations on the size and structure of the heater 220 than if the heater 220 were located at other locations, such as in or on the needle 202.

The distal end 240 of the needle 202 can have various structures that can allow the fluid in the input conduit 224 to heat the needle 202. One example structure of the distal end 240 is shown in FIG. 2C. In this example, a supply conduit 244 is positioned in shell 242 of the needle 202. The shell 242 can be shaped as a cylindrical member that terminates at a tip 246. The shell 242 can define a cavity into which the supply conduit 244 can be positioned. The input conduit 224 can be coupled to the supply conduit 244 to allow the fluid to flow from the input conduit 224 to the distal end 240 of the needle through the supply conduit 244. The fluid can then exit the supply conduit 244 proximate the tip 246 of the needle 202. The fluid can then flow back toward the handle and contact the shell 242. In this manner, thermal energy can be exchanged between the fluid and the shell 242. This allows the needle 202 to be heated or cooled as desired.

The return path of the fluid (as indicated by arrows on FIG. 2C) can be defined by an outer surface of the supply conduit 244 and an internal surface of the shell 242. This return path can then be coupled to the output conduit 226 at or near the handle 204. In this manner, a fluid pathway is defined through the needle from the heater 220 and back to the handle 204.

During a cooling cycle of the probe 200, a cryogen can flow through the input conduit 224, through the supply conduit 244 and back through the return pathway and back through the output conduit 226. The cryogen can have a suitably low temperature to remove heat from a target tissue positioned proximate the shell 242 and/or the distal end 240 of the needle 202. Ice forms at the distal end 240 producing an iceball that destroys the target tissue.

During a heating cycle of the probe 200, a fluid (in a liquid, gas, or mixed form) can be passed through the input conduit 224 while the heater 220 is activated. The heater 220 can heat the fluid as it moves past the heater 220. The heated fluid can move into the needle 202 toward the distal end 240 through the supply conduit 244. The heater fluid may contact the shell 242 to heat the tissue, ice or area surrounding the distal end 240 of the needle 202. In this manner, the tissue, ice or other surrounding area of the needle can be heated as desired. The fluid can then flow away from the distal end 240 along the return pathway and back through the output conduit 226 in the handle 204.

Figure 3:
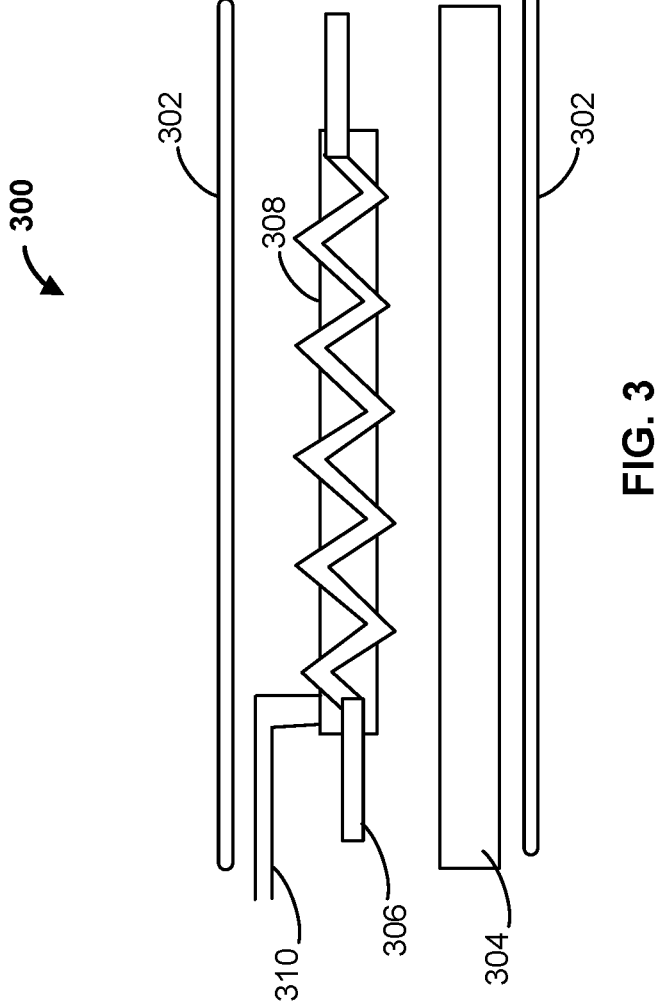
FIG. 3 is a side view of another example heater that can be positioned in the handle of the probe of FIG. 2A.

Turning now to FIG. 3, another example heater 300 is shown. The heater 300 may be positioned in the handle 204 of the probe 200. The heater 300 may operate similarly to the heater 220 previously described and be coupled to the supply conduit 244 and the return path as previously described to provide a cold cryogen for cooling cycles and a heated fluid for heating cycles.

In this example, the input conduit 306 may be configured as a loop or helix to wrap around a heating element 308. The cryogen and/or heating fluid may flow through this circuitous path. When the heating element 308 is activated, thermal energy from the heating element 308 may be transferred to the fluid flowing through the input conduit 206 to heat the fluid. The heated fluid can then be passed to the needle 202 for heating the needle 202 as previously described. The heating element 308 may be a resistive heating element that can heat when a power signal is passed to the heating element by the leads 310. The amount of thermal energy that is passed to the fluid can be controlled by controlling the duty cycle of the power signal provided to the heating element 308 via the leads 310. The leads 310 can be coupled a power source in the cryo controller 104, for example. In other examples, the heating element 308 can include a magnetic coil heater, a fiber laser heater or the like.

The heater 300 may be located in the housing 302 of the handle 204. The housing 302 can be similar to the housing 222 previously described. An output conduit 304 may also be positioned in the housing 302. The output conduit 304 can be coupled to the return path of the needle 202 to allow the cryogen and/or heating fluid to be returned from the needle 202.

As can be appreciated, the probes of the present disclosure such as probes 102, 200 can be used to perform cryoablation treatments that may include heating cycles. The heating cycles can be used in various circumstances to provide advantageous treatments and conditions that are improvements over existing and/or traditional probes and methods. In one circumstance, the probes of the present disclosure can be used to reduce the treatment time required to perform a cryoablation treatment. The probes can be used, for example, to create an iceball at a target tissue in a patient. After such ice has been formed and maintained for a sufficient time, it is desirable to remove the needle 202 from the patient. The needle 202, however, may be embedded in the iceball that forms around the needle 202. It can be desirable to heat the needle to melt the ice at the needle 202 to allow the needle to be removed.

It may be desirable to heat the needle 202 to a temperature of 70° C. or greater to quickly heat the needle 202 so that it can be removed. It may not be possible to achieve such temperatures using existing probes and methods. The probes of the present disclosure, however, can be used to heat the fluid using the heaters in the handle of the probe to raise the temperature of the fluid to heat the needle 202 to such temperatures. Thus, the ice can be quickly melted and the needle 202 can be removed from the patient to reduce a total time of the patient.

In some examples, the probes of the present disclosure can result in a decrease of 50% or more of thaw time over traditional probes. Some traditional probes may achieve temperatures to allow a needle to be removed from an iceball in about 60 seconds. Some probes of the present disclosure can heat sufficiently to allow the needle to be removed from the iceball in about 30 seconds. In other examples of the present disclosure, the probes can operate to allow a needle to be removed from an iceball in about 20 to about 30 seconds. In some such examples, the needle of the probe of the present disclosure can rapidly heat to temperatures in the range of about 120° C. to about 150° C. in about 30 seconds.

In another circumstance, a bleeding condition may occur during a cryoablation treatment. The tissue surrounding the needle 202 may bleed as a result of the needle being positioned in or around the tissue. It is desirable to minimize the amount of bleeding that occurs to minimize the impact of the treatment on the patient. The heaters of the present disclosure that are positioned in the handles of the probes can quickly heat the needle to a suitable temperature to promote the coagulation of blood if a bleeding condition occurs.

In other circumstances, it may be desirable to cauterize tissue and/or to denature proteins at the site at which the needle is positioned. In a first circumstance, the needle 202 may be positioned in a patient. Using imaging or other positioning information, it may be determined that the needle 202 needs to be moved to properly position the needle 202 at the target tissue in the patient. It can be desirable to minimize the amount of cells that are migrated between tissues when the needle 202 is moved. For example, it is desirable to minimize the amount of cancerous or other abnormal cells that are moved or migrated to surrounding healthy tissues. To minimize migration, the cells surrounding the needle can be denatured by heating the needle 202. The needle 202 can be quickly heated using the heater positioned in the handle to raise the temperature of the needle to a suitable temperature to denature the proteins at the needle. The needle 202 can then be moved while minimizing the risk of migration of abnormal cells to healthy tissues.

In another circumstance, it may be desirable to cauterize the tissue surrounding the needle 202 when the needle 202 is removed following an ablation treatment. The cauterization of tissues can minimize bleeding that may otherwise occur. It can be desirable, however, the stop such cauterization before the needle reaches the skin of the patient. It is desirable so that the skin and/or tissue below the skin is allowed to heal to close the wound caused by the insertion of the needle 202. If the heating is not stopped, the track of the needle can create a pathway for the ingress of contaminants into the patient. The cryoablation systems of the present disclosure can, therefore, quickly raise the temperature of the needle 202 (e.g., greater than 90° C.) to cauterize tissue when the needle 202 is removed but also sense when the needle has moved a sufficient amount and/or is located at a predetermined location relative to the skin of the patient to stop such heating and cauterization before the needle 202 exits the patient.

The cryoablation systems of the present disclosure can include real-time and closed loop feedback systems to control the operating conditions of the probe to provide improved ablation results. The measurement points 116, 210 on the probes 102, 200, respectively, can be used, for example, to collect information such as flow rates, pressures, temperatures, impedances, and the like during ablation treatments. This information can be used to determine whether the probe is operating in a manner to achieve a desired result. For example, the probes of the present disclosure can automatically adjust to perform cooling cycles, heating cycles, thaw cycles, coagulation cycles, denaturing cycles, and the like according to predetermined treatment plan. The treatment plan can be determined prior to the treatment either automatically or in conjunction with a medical professional or technician based on the size, type, location of a target tissue and on aspects of the patient and desired results.

In yet other example embodiments in accordance with the present disclosure, a probe may be configured similarly to the probe 200 previously described. In addition to the heater 220, other heaters may be provided to heat the heating fluid and/or the needle 202. In some such examples, a second heater may be located in the needle 202 at or near the distal end 240. The second heater may be a resistive heater or other heater that can be the same as heater 220 or heater 230 or different from the heater 220 or heater 230. In other examples, multiple heaters 220 may be included in the handle and multiple heaters may be included in the needle 202. Still further, heaters may also be located in thermal communication with the heating fluid outside of the handle 220, such as in cryo controller 104 and/or in heating system 108. Such multiple heaters may be controlled to sequentially or independently heat the heating fluid as needed to reach a desired temperature of the needle 202.

Figure 4:
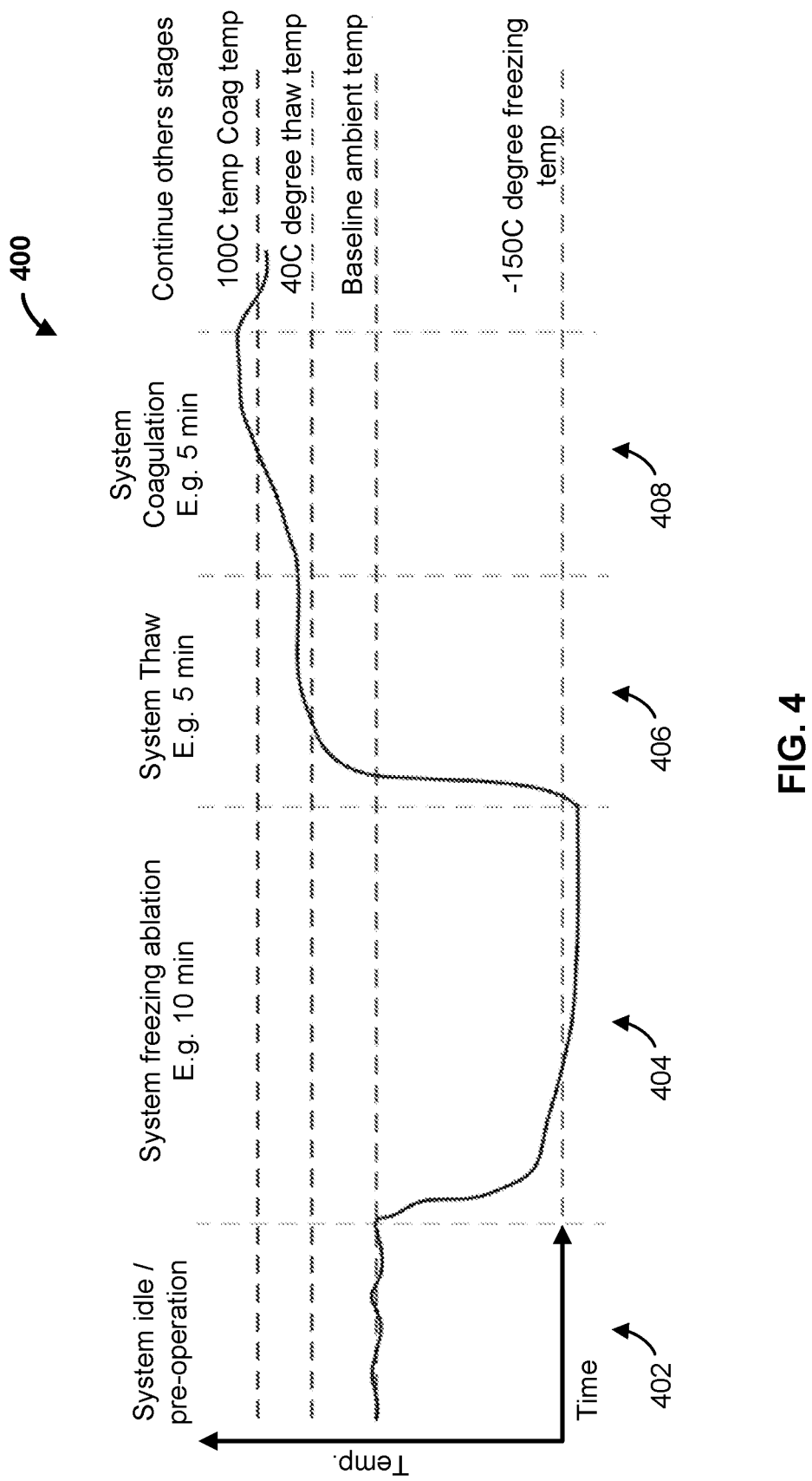
FIG. 4 is a graph illustrating an example temperature profile that can be achieved with a probe and/or systems of the present disclosure.

Referring now to FIG. 4, an example graph 400 is shown that illustrates an example cryoablation treatment in which the temperature of the distal end of the probe is plotted versus time. In a first zone 402, the cryoablation system is in a system idle or pre-operation state. The probe may be inserted in the patient and an initial or baseline temperature of the probe is monitored. When the stability of the probe and the position of the probe is confirmed through imaging or other positioning sensors, the cryoablation system may move to the system freezing cycle 404.

During the system freezing cycle 404, a cryogen may be passed to the needle of the probe to form ice at the target tissue. As shown, the cryogen may cause the temperature of the probe to quickly drop to temperature of −150° C. or less. The freezing cycle 404 may last for a sufficient time during which the iceball may form to a sufficient size to destroy the target tissue. When the iceball is of a sufficient size and/or a sufficient time has elapsed, the cryoablation system may move to a system thaw cycle 406.

During the system thaw cycle 406, the heating fluid can be passed through the handle of the probe where thermal energy is passed to the heating fluid from the heater. The heating fluid can then flow to the distal end of the needle to heat the needle. As shown, the probes of the present disclosure can quickly heat the needle to temperature in excess of 40° C. or higher, to thaw the ice and allow the needle to be removed from the iceball. When the time for system thaw 406 has passed, the cryoablation system can perform a system coagulation cycle 408.

During the system thaw 406, the tissues surrounding the needle may begin to bleed. To promote coagulation in the system coagulation cycle 408, the temperature of the tissue is desirably elevated. As shown, the probes of the present disclosure can quickly raise the temperature of the probe to a temperature of 100° C. or greater. This can promote coagulation.

After the cycles shown, the cryoablation system may perform other cycles or other stages. For example, freezing cycles may be re-performed or other heating cycles may be performed. The treatment plan for a cryoablation treatment may include multiple freezing and multiple thaw cycles, for example.

Figure 5:
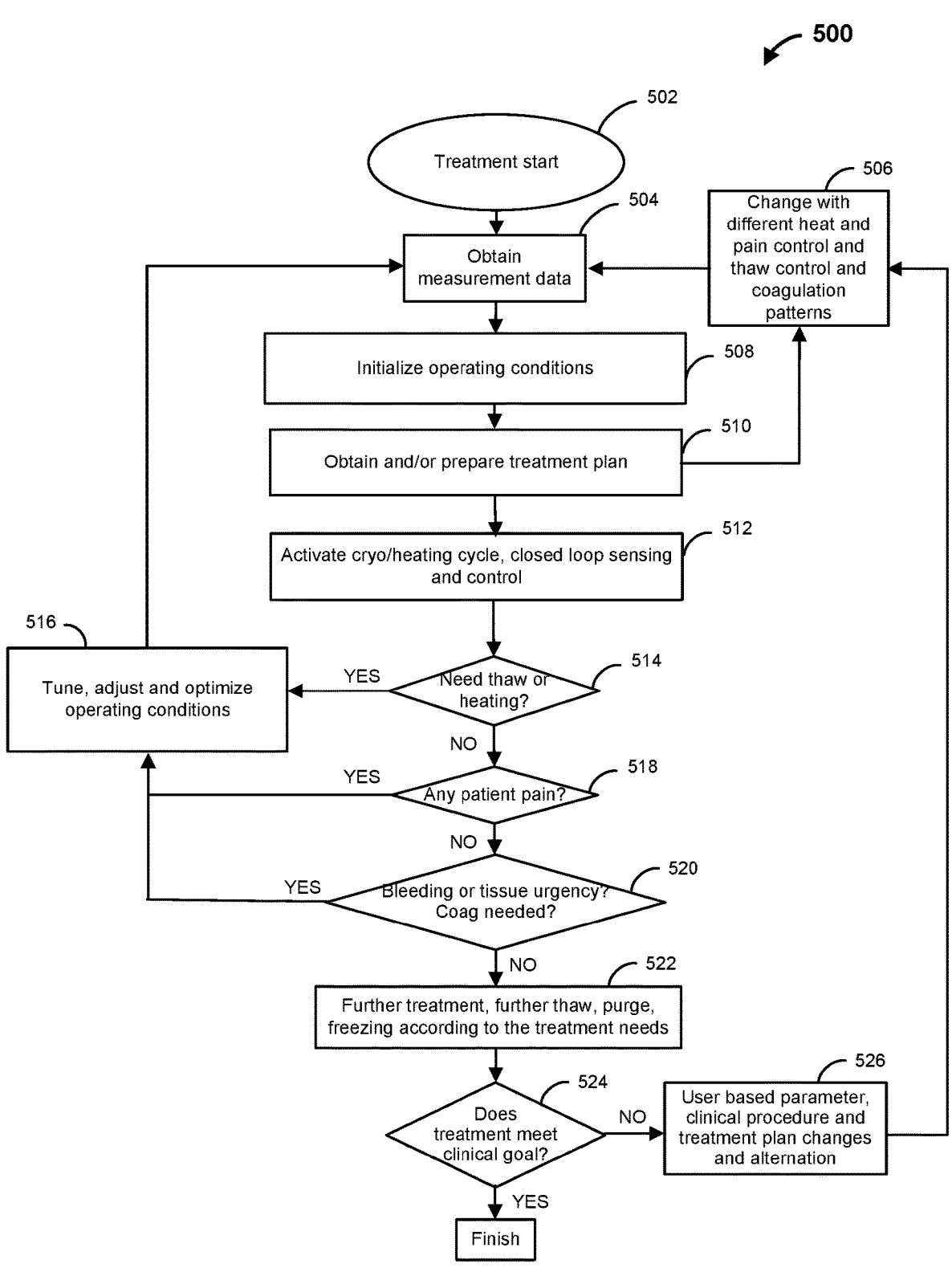
FIG. 5 is a flow chart illustrating an example method of performing an ablation treatment in accordance with some embodiments of the present disclosure.

Referring now to FIG. 5 an example method 500 of performing an ablation treatment is shown. The method 500 may be performed using one of the cryoablation systems of the present disclosure, including cryoablation system 100. While the cryoablation system 100 and the probes 102, 200 may be used in the description below, it should be appreciated that other cryoablation systems can also be used.

The method 500 may begin at step 502. At step 502, the probe 200 may be inserted into the patient and its position may be confirmed using imaging or other positioning methods. After positioning is confirmed, the method 500 may move to step 504.

At step 504, the cryoablation system 100 may obtain measurement data. The measurement data may include temperature, impedance, image, pressure, flow and other monitoring of conditions of the patient and of the cryoablation system 100. At step 504, impedance and temperature data collection may occur. The impedance and temperature data may be collected from the probe 200 via the measurement points 210. The probe 200 may include pads and/or sensors that can collect temperature and impedance measurements. The measurement data can be sent to or obtained by the cryo controller 104.

At step 508, the cryoablation system 100 can be initialized with predetermined or initial operating parameters. Such parameters may be determined as part of a treatment plan that can be obtained by the cryo controller 104. The various parameters such as the characteristics of the cryogen or heating fluid, temperatures of the fluids, pressures of fluids, flow rates of the fluids, and the like may be included in the initial operating parameters.

At step 510, the treatment plan can be obtained. A user may interface with the cryo controller 104 using a user interface on the ablation computing device 102, for example. The ablation computing device 102 may obtain the treatment plan from a health records database or other source, in other examples. The user may modify, change, or adjust the treatment plan and/or may modify the operating parameters of the cryoablation system 100 as may be desired. In some instances, the treatment may be initiated and move to step 512. In other instances, the method 500 may proceed to step 506.

The method 500 may move to step 506 when the circumstances of particular treatment such as the tissue conditions, the conditions of the patient (e.g., pain and health), or other conditions indicate that the treatment plan needs further modification or revision. In such instances, the treatment plan can be revised and input to the cryo controller 104. Such changes may include different ablation and/or pain control methods and/or other treatment modifications. According to clinical application and user needs, e.g. the tissue location, impedance, blood flow, temperature, tissue material (muscle, fat, bone, etc.), different ablation parameters may be utilized, such as cryo ablation pressure/duration, on/off time, duty cycle, etc., can be automatically and adaptively adjusted and manipulated according to user feeling (such as comfortness index) and medical professional feedback (operation time, temp estimation, ice ball size estimation, pain level, etc.). Additionally, some of the parameters' control may be based on a calculation index, such as impedance changes, temperature change rate, and patient pain level changes, etc. After step 506, the method 500 can return to step 504 and proceed as described.

If the method proceeds to step 512 after step 510, the treatment may be initiated and a cryo cycle may be initiated. In addition, closed loop sensing and control can activated. At step 512, the cryo controller 104 may control the flow a cryogen, flow of the heating fluid, activation of the heater 220 and other operating conditions of the cryoablation system 100. The cryo controller 104 can determine whether such conditions may be occurring such as patient pain, bleeding conditions, iceball formation, and the like.

At step 514, the cryo controller 104 may determine whether a thaw or heating cycle is required. The cryo controller 104 may determine whether a thaw or heating cycle is required. Such determination may be made using the treatment plan. The treatment plan may prescribe a heating or thaw cycle. In other examples, the cryo controller 104 may determine that a heating cycle is required automatically by sensing a temperature or other condition of the probe 200. If a heating or thaw cycle is required the method may move to step 516. If no heating or thaw cycle is required, the method 500 may move to step 518.

At step 516, the cryo controller 104 may adjust the operating parameters of the cryoablation system 100. For example, the cryo controller may stop the flow of cryogen and then initiate a heating cycle by initiating a flow of heating fluid and/or activating the heater 220. After step 516, the method 500 may return to step 504 to re-perform the steps of method 500 as previously described. In this manner, the cryo controller 104 can perform actions to follow a treatment plan.

At step 518, the cryo controller 104 may determine whether a pain condition is observed with the patient. For patient pain level and comfort level, different parameters and/or indexes may be used, determined or developed based on the clinical needs and medical professional estimation. Patient feedback for pain level may be used during a procedure to adjust the operation parameters, such as length of freezing or heating cycles, frequency and temperature. In addition, various measurements and/or indicators may be used to determine pain level or a pain condition. Such indicators may include patient heart rate, muscle response, facial reflection, breath rate, etc. These indicators and/or other vital signs and patient response mechanical and bio-electrical signals can also be utilized for patient pain and comfortness level determination and quantification. Such measurements, indicators, and signals may be compared to predetermined levels, ranges or other thresholds to determine if a pain condition is present. If a pain condition is detected, the method 500 may move to step 516. If no pain condition is present, the method 500 may move to step 520.

At step 516, the cryo controller 104 may make changes, modification or other revisions to the operating conditions of the cryoablation system 100 to address the pain condition. For example, the cryo controller 104 may change a temperature or length of freezing or heating cycle. In other circumstances, the cryo controller 104 may initiate a heating cycle to reduce pain. After such change, adjustment, and/or remedial action is taken by the cryo controller at step 516, the method 500 may return to step 504 to re-perform the steps of method 500 previously described. Thus, the cryoablation system 100 can also take action to alleviate pain conditions in addition to the other functionality described.

At step 520, the cryo controller 104 may determine whether a bleeding condition or other tissue condition exists. Whether a bleeding condition is occurring may be made, for example, using the impedance measurements obtained from the probe 200. A bleeding condition can be determined, for example, by comparing the impedance measurement to a predetermined bleeding impedance range. Bleeding conditions may also be determined by measuring a change in impedance and comparing the change in impedance to predetermined range or threshold. If tissue bleeding is observed, the method 500 can move to step 516. If no tissue bleeding is observed, the method 500 can move to step 522.

At step 516, the cryo controller 104 may initiate a heating cycle to address the bleeding or other tissue condition determined at step 520. For example, the cryo controller 104 may initiate a flow of heating fluid and activate the heater 220. After step 516, the method 500 may return to step 504 to re-perform the step s of method 500 as previously described.

At step 522, further treatment, further thaw, purge or freezing cycles may be performed. The treatment plan, for example, may detail repeated freezing cycles and/or repeated heating cycles. The particular needs and conditions of the tissue and the patient can dictate the details of the treatment plan.

At step 524, the cryo controller 104 may determine whether the treatment meets the clinical goal. The cryo controller 104 may make this determination by comparing measurement data to anticipated measurement data. Imaging data may also be collected that may measure aspects of the treatment such as location of the probe 200, size and location of an iceball, and/or other aspects of the treatment. This information can be used to determine whether the treatment meets the clinical goal. If the clinical goal has been met, the method can end. If the clinical goal has not been met, the method may proceed to step 526.

At step 526, the treatment plan, operating parameters, and/or clinical procedure can be changed. The cryo controller 104 and/or the ablation computing device 102 may recommend such changes and present such recommendations to a user or medical professional. The method may move to step 506 after step 526 to implement such recommendations and/or changes to the treatment plan, operating parameters, and/or the clinical treatment. The method may then return to step 504 to re-perform the steps as previously described except with the changes determined at step 526 and/or step 506.

Figure 6:
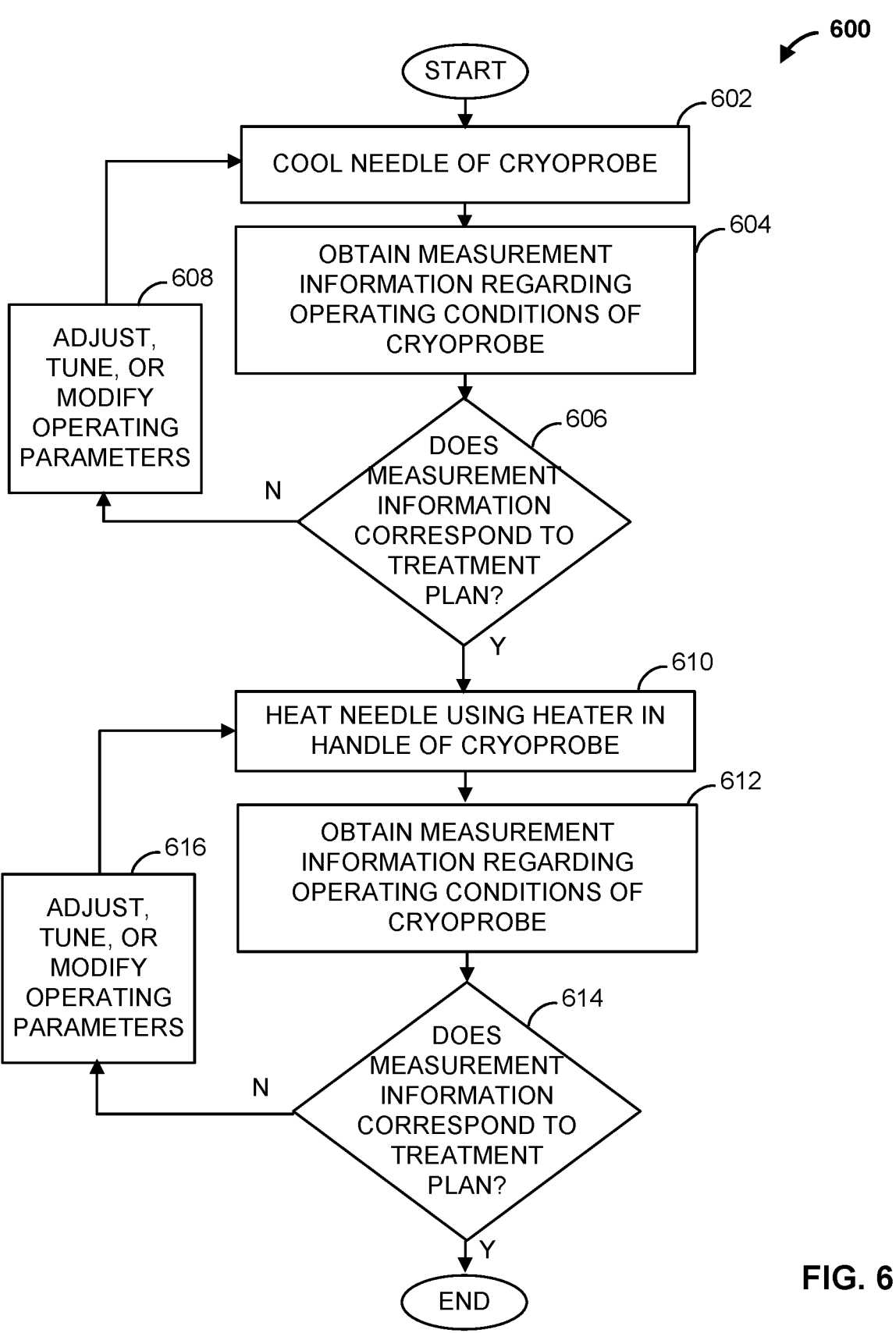
FIG. 6 is a flow chart illustrating another example method of performing an ablation treatment in accordance with some embodiments of the present disclosure.

Referring now to FIG. 6, another example method 600 of performing a cryoablation treatment is shown. The method 600 may be performed, for example, using the various systems and probes described in the present disclosure such as cryoablation system 100 and probes 102, 200. It should be appreciated, however, that other systems and devices can also be used.

The method 600 begins at step 602. At step 602, the cryo controller 104 may initiate cooling of the needle 202 of the probe 200. The cryo controller 104 may have obtained a treatment plan or other instructions that may describe the operating conditions for the ablation treatment. The treatment plan or other instructions may describe an initial set of operating parameters of the cryoablation system 100. The needle 202 of the probe 202 may be positioned at or near the target tissue in the patient. The cryo controller 104 may begin moving cryogen through the probe 200 to the needle 202 to begin cooling of the needle. During this freezing cycle, ice may be formed at the target tissue.

At step 604, the cryo controller 104 may obtain measurement information regarding operating conditions of the cryoprobe. The cryo controller 104 may obtain measurement information from the measurement points 210, for example. The cryo controller 104 may also obtain measurement information from other diagnostic devices, imaging devices, sensors, and other equipment that can provide information regarding conditions of the patient, performance of the probe 200, conditions of the probe 200, and the like. The measurement information may include, for example, impedance measurements, temperature measurements, pressure measurements, flow measurements, etc. This information can be obtained by the cryo controller 104 from the probe 200 or other devices via wired or wireless connections.

At step 606, the cryo controller 104 and/or the ablation computing device 102 can compare the measurement information to the treatment plan. The comparison can determine whether the treatment is proceeding as anticipated. For example, the temperature of the needle 202 can be compared to a predetermined temperature threshold and/or to a predetermined temperature range. The size, temperature, and location of the iceball that forms as a result of the cryogen flowing through the needle 202 of the probe 200 can be compared to desired or predetermined size, temperature, and location. If the measurement information corresponds to the treatment plan, the method 600 can move to step 610. If the measurement information does not correspond to the treatment plan, the method 600 can move to step 608.

At step 608, the cryo controller 104 can adjust, tune, or modify operating parameters of the cryoablation system 100. The cryo controller 104 and/or the ablation computing device 102 can alert the user and/or cause a message to be displayed to inform the user that an adjustment is required. The cryoablation system 100 may, for example, adjust a flow rate, pressure, or other characteristic of the cryogen that is being provided to the needle 202 of the probe 200. Such an adjustment may be made to increase the growth and/or growth rate of the iceball being formed, for example. As can be seen, the method 600 and the systems and probes of the present disclosure allow the cryoablation system 100 to operate in a closed-loop manner to monitor and adjust the operation of the system in response to feedback received in real-time during an ablation treatment.

At step 610, the cryo controller 104 may initiate a heating cycle and heat the needle 202 of the probe 200. The cryo controller 104 may heat the needle using a heater that is positioned in the handle of the probe 200 as previously described. The cryo controller 104 may activate the heater 220 in the handle and initiate a flow of heating fluid to the needle 202. As the heating fluid flows to the needle 202, the heater 220 can quickly heat the heating fluid that, in turn, can transfer thermal energy to the needle 202. The heating of the needle at step 610 can be performed in various circumstances and for various reasons as previously described. The heating of the needle at step 610 can be performed, for example, to promote coagulation, to denature proteins in cells proximate the needle, to allow the needle to be moved from the iceball, to relieve pain, or for other reasons and circumstances.

At step 612, the cryo controller 104 can obtain measurement information regarding operating conditions of the probe 200. The measurement information can be similar to the measurement information obtained at step 604. The measurement information can be obtained from the probe 200 and/or from other sensors, imaging devices, monitoring equipment, patient health measurement devices, and the like. The measurement information can, for example, obtain information regarding the heating occurring at the needle 202, such as temperature, impedance, pressure, flow rates, and the like.

At step 614, the cryo controller 104 and/or the ablation computing device 102 can compare the measurement information to the treatment plan to determine if the measurement information corresponds to the treatment plan. The comparison at step 614 may be similar to the operations described above with respect to step 606. The cryo controller 104 and/or the ablation computing device can compare the measurement information to thresholds, ranges, or other targets that may be included in the treatment plan. If the measurement information corresponds to the treatment plan, the method 600 may end. If the measurement information does not correspond to the treatment plan, the method 600 may move to step 616.

In various examples, the treatment plan or other information used to control the operation of the cryoablation system 100 may control the temperature of the heating fluid to control a temperature of the needle 200 so that the needle 202 is maintained in a desired operating range according to the treatment needs. For example, if the heating cycle is performed for a thaw cycle, the predetermined temperature range may be in the range of about 5° C. to about 15° C. If the heating cycle is performed to promote coagulation of blood in the case of bleeding, the predetermined temperature range may be in the range of about 40° C. to about 70° C. If the heating cycle is performed for track ablation (e.g., when needle is removed from tissue), the predetermined temperature range may be in the range of about 50° C. to about 90° C. If the heating cycle is performed for cauterization of tissue (e.g., to burn and/or destroy cancer cell/tissue or other abnormal cell/tissue), the predetermined temperature range may be in the range of about 80° C. to about 120° C. for soft tissue (e.g., kidney, lung, etc.) or about 120° C. to about 150° C. for rigid tissue (e.g., bone). In other examples, other temperature ranges may be used and/or may be programmed and adaptively controlled according to a target tissue.

At step 615, the cryo controller 104 may adjust, tune, or modify one or more operating parameters of the cryoablation system 100. The cryo controller 104 may, for example, desire to increase or decrease the thermal energy being transferred to the needle 202. The cryo controller 104 may modify a flow rate, pressure, temperature, or other characteristic of the heating fluid that is being provided to the needle 202. The cryo controller 104 may activate or de-activate the heater 220 at step 616. As can be seen, the cryoablation system 100 may operate as a closed-loop feedback system to monitor and adjust operating conditions so that the ablation treatment can be optimized. Such optimization can improve the efficacy of the treatment, reduce a treatment time for the procedure, and/or reduce the likelihood of damaging or harming healthy tissues.

As can be appreciated, the method 600 may be repeated multiple times during a single treatment or the freezing cycles and/or heating cycles may be repeated during a single treatment. Furthermore, the method 600 may include further steps that can be used to determine when a heating cycle may be performed and/or a length or duration of a heating cycle.

In one such example method (not shown), the cryoablation system 100 may be used in a circumstance when the needle 202 is removed from a patient. It may be desirable to denature proteins at cells in the target tissue to reduce migration of abnormal cells and to cauterize tissues to reduce bleeding that may occur. The needle 202 may be used to denature proteins and/or cauterize tissues when the needle is removed. The cryo controller 104 may initiate a heating cycle and heat the needle to a suitable temperature (e.g., greater than or equal to 90° C.) to provide this functionality. The cryo controller 104 may activate the heater 220 and deliver heating fluid through the handle 204 of the probe 200 to heat the heating fluid in the handle 204. The heated fluid can then flow to the needle 202 to rapidly heat the needle 202 to the desired temperature. Once the desired temperature is reached, the needle 202 can be extracted.

As the needle 202 is extracted, the heated needle 202 can denature proteins and/or cauterize tissues in the needle's track. It is desirable to stop the denaturing and/or cauterization before the needle is fully removed from the patient's skin so as to allow healing and closing of the skin to prevent or reduce a likelihood of internal contamination. The probe 200 may be used to automatically stop the heating cycle and bring the temperature of the needle 202 down to a desired temperature to stop cauterization of tissue.

In some examples, the measurement points 210 can detect when the distal end of the needle 202 is nearing the patient's skin. An impedance, temperature or other measurement can be used for this purpose. When the cryo controller 104 detects such a position of the needle 202, the cryo controller 104 can cease a flow of heating fluid and/or de-activate the heater 220. Such action can allow the needle's temperature to reduce to a desired temperature level. In other examples, the probe 200 may be equipped with a proximity sensor that can be located on the handle 112 that can detect a position of the handle relative to the patient's skin. The feedback from the proximity sensor can be used to de-activate the heating cycle before the needle 202 is removed from the patient's skin. In other examples, other sensors and/or measurements can be used.

Figure 7:
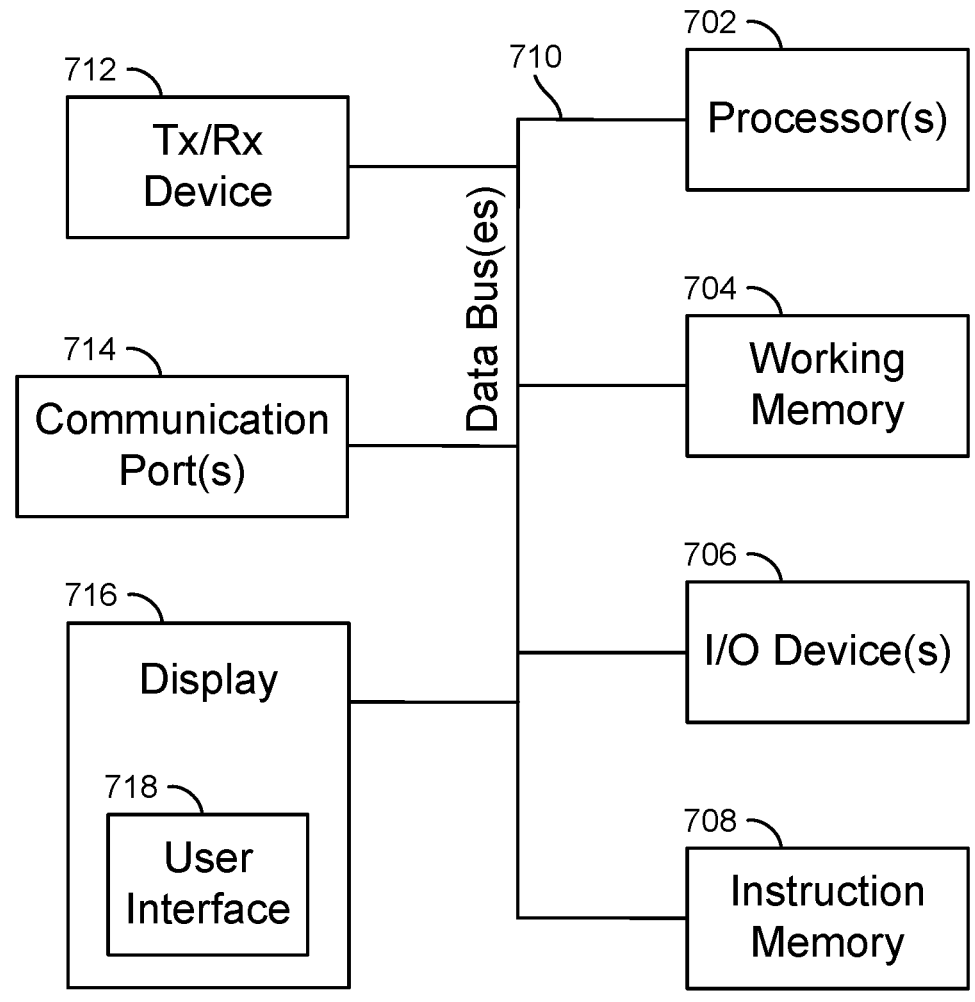
FIG. 7 is a diagram illustrating an example computing device that can be used in one or more ablation systems of the present disclosure.

Referring now to FIG. 7, an example computing device 700 is shown. The cryoablation system 100 may include one or more computing devices 700. For example, the cryo controller 104 and/or the ablation computing device 102 may have the elements shown in FIG. 7. The methods of the present disclosure, such as methods 500, 600 may be performed, or steps of such methods may be performed, by a computing device 700.

As shown, the computing device 700 may include one or more processors 702, working memory 704, one or more input/output devices 706, instruction memory 708, a transceiver 712, one or more communication ports 714, and a display 716, all operatively coupled to one or more data buses 710. Data buses 710 allow for communication among the various devices. Data buses 710 can include wired, or wireless, communication channels.

Processors 702 can include one or more distinct processors, each having one or more cores. Each of the distinct processors can have the same or different structure. Processors 702 can include one or more central processing units (CPUs), one or more graphics processing units (GPUs), application specific integrated circuits (ASICs), digital signal processors (DSPs), and the like.

Processors 702 can be configured to perform a certain function or operation by executing code, stored on instruction memory 708, embodying the function or operation. For example, processors 702 can be configured to perform one or more of any function, step, method, or operation disclosed herein.

Instruction memory 708 can store instructions that can be accessed (e.g., read) and executed by processors 702. For example, instruction memory 708 can be a non-transitory, computer-readable storage medium such as a read-only memory (ROM), an electrically erasable programmable read-only memory (EEPROM), flash memory, a removable disk, CD-ROM, any non-volatile memory, or any other suitable memory.

Processors 702 can store data to, and read data from, working memory 704. For example, processors 702 can store a working set of instructions to working memory 704, such as instructions loaded from instruction memory 708. Processors 702 can also use working memory 704 to store dynamic data created during the operation of ablation computing device 102. Working memory 704 can be a random access memory (RAM) such as a static random access memory (SRAM) or dynamic random access memory (DRAM), or any other suitable memory.

Input-output devices 706 can include any suitable device that allows for data input or output. For example, input-output devices 706 can include one or more of a keyboard, a touchpad, a mouse, a stylus, a touchscreen, a physical button, a speaker, a microphone, or any other suitable input or output device.

Communication port(s) 714 can include, for example, a serial port such as a universal asynchronous receiver/transmitter (UART) connection, a Universal Serial Bus (USB) connection, or any other suitable communication port or connection. In some examples, communication port(s) 714 allows for the programming of executable instructions in instruction memory 708. In some examples, communication port(s) 714 allow for the transfer (e.g., uploading or downloading) of data, such as measurement information and the like.

Display 716 can display a user interface 718. User interfaces 718 can enable user interaction with the ablation computing device 102. For example, user interface 718 can be a user interface that allows an operator to interact, communicate, control and/or modify different messages, settings, or features that may be presented or otherwise displayed to a user. The user interface 718 can include a slider bar, dialogue box, or other input field that allows the user to control, communicate or modify a setting, limitation or input that is used in a cryoablation treatment. In addition, the user interface 718 can include one or more input fields or controls that allow a user to modify or control optional features or customizable aspects of the ablation computing device 102 and/or the operating parameters of the cryoablation system 100. In some examples, a user can interact with user interface 718 by engaging input-output devices 706. In some examples, display 716 can be a touchscreen, where user interface 718 is displayed on the touchscreen. In other examples, display 716 can be a computer display that can be interacted with using a mouse or keyboard.

Transceiver 712 allows for communication with a network. In some examples, transceiver 712 is selected based on the type of communication network ablation computing device 102 will be operating in. Processor(s) 702 is operable to receive data from, or send data to, a network, such as wired or wireless network that couples the elements of the cryoablation system 100.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for performing a cryoablation treatment comprising:

a probe comprising:

a handle comprising an input conduit, an output conduit, and a heater, the heater positioned in thermal communication with the input conduit; and a needle having an outer diameter of 1.2 mm or less and connected to the handle and extending therefrom to a distal end, the needle comprising a supply conduit fluidly coupled to the input conduit and a return path, the supply conduit and the return path defining a fluid pathway through the needle, the fluid pathway configured to move a fluid therethrough to alternatively cool and heat the needle; and one or more ablation computing devices coupled to the probe, the one or more ablation computing devices configured to selectively heat and cool the needle; wherein:

the one or more ablation computing devices are further configured to selectively activate the heater to heat the needle to multiple different predetermined temperature ranges; and each of the predetermined temperature ranges corresponds to a heating range configured to perform a thaw cycle, a cautery cycle, a track ablation cycle, and a coagulation cycle.

2. The system of claim 1, wherein the fluid pathway is configured to move a cryogen, and the probe is configured to alternatively cool the needle when the heater is not activated and to heat the needle when the heater is activated.

3. The system of claim 1, wherein the supply conduit is positioned inside a shell of the needle and the return pathway is defined by an outer surface of the supply conduit and an inner surface of the shell.

4. The system of claim 3, wherein the shell has an outer diameter of 1.0 mm or less.

5. The system of claim 3, wherein the handle further comprises an output conduit fluidly coupled to the return path.

6. The system of claim 1, wherein the handle encloses the heater and the needle has an outer diameter of 1.0 mm or less.

7. The system of claim 1, wherein the heater is positioned around the input conduit.

8. The system of claim 1, wherein the input conduit is positioned around the heater.

9. The system of claim 1, wherein the heater comprises a resistive heater.

10. The system of claim 1, wherein the heater comprises one of a magnetic heater and a fiber laser heater.

11. The system of claim 1, further comprising one or more measurement points positioned on the needle.

12. The system of claim 11, wherein the one or more measurement points comprise temperature sensors configured to determine a temperature of the needle.

13. The system of claim 1, wherein the one or more ablation computing devices are configured to activate the heater when a bleeding condition is detected.

14. The system of claim 1, wherein the one or more ablation computing devices are configured to activate the heater when the needle is being moved from a treatment position in a patient and to de-activate the heater when the needle has been moved a predetermined distance from the treatment position.

15. A method comprising:

cooling the needle of the probe in the system of claim 1 to form ice at a target tissue; and heating the needle of the probe using the heater positioned in the handle of the probe.

16. The method of claim 15 wherein the step of heating the needle of the probe comprises heating the fluid that moves through the handle to the distal end of the needle, the fluid in thermal communication with the heater in the handle of the probe.

17. The method of claim 15, wherein the step of cooling the needle comprises moving a cryogen from a cryogen source through the handle and toward the distal end of the needle.

18. The method of claim 15, further comprising:

obtaining measurement information regarding operating conditions of the probe;

comparing measurement information to a treatment plan; and adjusting the operating conditions of the probe if the measurement information deviates from the treatment plan.

19. The method of claim 15, wherein the step of heating the needle comprises denaturing proteins in tissue proximate the needle to reduce a likelihood of contaminating healthy tissues.

20. The method of claim 15, wherein the step of heating the needle is performed after the step of cooling the needle in order to allow the needle to be removed from the ice.

21. The method of claim 15, wherein the step of heating the needle is performed to promote coagulation of blood when a bleeding condition is detected.

22. The method of claim 15, wherein the step of heating the needle is performed when the needle is moved from a first position to a second position.

23. The method of claim 22, wherein the step of heating the needle is initiated when the needle is positioned at an initial position at the target tissue, and the heating of the needle is automatically stopped when the needle is moved a predetermined distance.

5

\* \* \* \* \*